(12) United States Patent
Brar

(10) Patent No.: US 8,176,590 B1
(45) Date of Patent: May 15, 2012

(54) OSCILLATING TOOTHBRUSH

(75) Inventor: Balbir S. Brar, Laguna Hills, CA (US)

(73) Assignee: Balbir S. Brar, Laguna Hills, CA (US)

( * ) Notice: Subject to any disclaimer, the term of this patent is extended or adjusted under 35 U.S.C. 154(b) by 0 days.

(21) Appl. No.: 12/890,044

(22) Filed: Sep. 24, 2010

(51) Int. Cl.
*A46B 13/02* (2006.01)

(52) U.S. Cl. .......................... 15/22.1; 15/22.2; 15/167.1

(58) Field of Classification Search .................... 15/22.1, 15/2.2, 167.1, 167.2, 22.2
See application file for complete search history.

(56) References Cited

U.S. PATENT DOCUMENTS

| | | | |
|---|---|---|---|
| 4,224,710 A | 9/1980 | Solow | |
| 4,795,347 A | 1/1989 | Maurer | |
| 5,148,567 A * | 9/1992 | Daub | ............................. 15/22.1 |
| 5,365,624 A | 11/1994 | Berns | |
| 5,572,762 A * | 11/1996 | Scheiner | ........................ 15/105 |
| 6,397,860 B1 | 6/2002 | Hill, II | |
| 6,821,119 B2 * | 11/2004 | Shortt et al. | ................... 433/118 |
| 7,354,448 B2 | 4/2008 | Altshuler et al. | |
| 7,444,709 B1 | 11/2008 | Chu | |
| 7,972,136 B2 * | 7/2011 | Hegemann | ...................... 433/80 |
| 2007/0009856 A1 | 1/2007 | Jones et al. | |
| 2008/0010770 A1 | 1/2008 | Hegemann et al. | |
| 2009/0056044 A1 | 3/2009 | Rizoiu et al. | |

* cited by examiner

*Primary Examiner* — Shay Karls
(74) *Attorney, Agent, or Firm* — Stout, Uxa, Buyan & Mullins, LLP; Donald E. Stout

(57) ABSTRACT

Unique dental care devices, systems and methods for cleaning teeth and oral tissue comprises an oscillating tooth brush with dual opposing brush heads, adapted to clean teeth and sulcus area. The devices are capable of brushing a set of opposing upper and lower teeth of the mouth simultaneously. The devices, once inserted and positioned into the mouth to clean a pair or a set of opposing upper and lower teeth, can be maneuvered inside the mouth cavity from one side of the mouth to the other to clean all the teeth without requiring removal from the mouth and repositioning.

16 Claims, 8 Drawing Sheets

OSCILLATING TOOTHBRUSH

BACKGROUND OF THE INVENTION

In order to address the important need to clean teeth, gums and certain parts or the entire mouth area to maintain oral hygiene, a number of manual and automated tooth and gum cleaning devices have been developed, including electric toothbrushes, oral irrigators and automated flossers. However, certain deficiencies remain with various such devices. Manual toothbrushes, for instance, require the user to have a certain minimum, moderate degree of manual dexterity in order to achieve proper brushing. Conventional electric or mechanical toothbrushes, while often requiring less physical effort and dexterity than manual toothbrushes, still require accurate human manipulation in order to achieve effective cleaning. Additionally, current brushing systems do not adequately clean molars and pre-molars, both uppers and lowers. Both a difficult reach, and a lack of adequate time for proper brushing are factors that cause the molars and pre-molars area of the mouth to be prevalent disease areas.

The present invention is presented as overcoming one or more of the above-mentioned drawbacks of the past oral and/or dental care devices and provides an effective means of oral and/or dental care for people of all ages, including those with natural teeth or with implants, crowns, braces and bridgework, as well as for people with limited dexterity, or having other handicaps.

SUMMARY OF THE INVENTION

This invention relates generally to a dental care device for cleaning teeth and oral tissue, and more particularly to an oscillating tooth brush with dual opposing brush heads, adapted to clean teeth, including the sulcus area. Specifically, the present invention involves unique teeth cleaning devices, systems, and methods for cleaning teeth and oral tissue. Although there are toothbrush devices with dual brush heads, these devices are awkward and either cannot be or cannot easily be manipulated to brush both the upper and lower teeth at the same time, particularly, all the teeth in a single cleaning operation that does not require removing and repositioning the toothbrush once inserted into the mouth. Accordingly, in one aspect of the invention, there is provided a toothbrush that brushes a pair or set of opposing upper and lower teeth of the mouth at the same time. In addition, the toothbrush, once inserted and positioned into the mouth to clean a pair or a set of opposing upper and lower teeth, can be maneuvered inside the mouth cavity from one side of the mouth to the other to clean all the teeth without requiring removal of the toothbrush from the mouth and repositioning of the toothbrush. Of course, the inventive system is also sufficiently versatile to be effective used to clean only the upper teeth or only the lower teeth, if desired.

The scope of the present invention extends beyond the non-limiting examples set forth herein and encompasses that which would be or should be within the purview of one having ordinary skill in the art of oral and/or dental care devices and toothbrushes.

As described elsewhere herein, the present invention encompasses manual and mechanically driven toothbrushes. Accordingly, various means of providing oscillating up and down motion to the brush heads that are obvious to a person of ordinary skill in the art of toothbrushes and oral and dental devices are also encompassed within the scope of the present invention. For example, means encompassed in the present invention include vibrating rods or strings or reciprocating cams or gears. In one embodiment, the brush heads are driven by an offset cam attached to an electric motor. As the motor revolves, it rotates the cam inside an enclosed shell which is attached to a flexure. In another embodiment, the brush heads can oscillate using electromagnetic radiation (EMR).

The devices of the present invention comprise dual opposing brush heads connected or detachably connected via a flexure to one end of a toothbrush handle.

The flexure in the present invention is substantially rigid, yet sufficiently flexible to permit gentle up and down movement of the brush heads when activated, as described elsewhere herein. In one embodiment, the flexure is a substantially planar or a substantially flat piece. In another embodiment, the flexure is a generally flat piece and at least a portion of the flexure is substantially planar or substantially flat. The generally flat and/or substantially flat or planar nature of even a portion of the flexure may permit the flexure to be substantially rigid, yet flexible to allow for gentle up and down movement of the flexure and, therefore the brush heads, in the plane of the flat side of the flexure. Furthermore, the flexure may comprise a part that is exposed to the user where it is linked to the upper and lower brush heads, and a part that is unexposed to the user in the assembled device that extends into the handle along the axis of the handle. Preferably, the flexure may be substantially planar or substantially flat or at least have a portion that is substantially planar or substantially flat at the unexposed part that extends into the handle along the axis.

The flexure described herein may be either flexible or rigid in nature. In the embodiment where the flexure is flexible, it is preferably flexible in only one direction, preferably in the plane intersecting the flexure and the two brush heads that allows for up and down motion of the brush heads in the plane intersecting the flexure and brush heads. The flexure may be flexible throughout or only in some portions or areas or parts, such as for example, in the unexposed part, or, for example, in the exposed part, and is preferably flexible in only one direction, preferably in the plane intersecting the flexure and the two brush heads, that allows for up and down motion of the brush heads in the plane intersecting the flexure and brush heads. Such flexibility is advantageous in making the action of teeth brushing or gum massaging thorough yet gentle and comfortable for the user as opposed to mechanical vibration from rigidly held brush heads which can be very overpowering and aggressive, and therefore may be uncomfortable for the user. Therefore such flexibility in the flexure allows for up and down movement in the plane intersecting the flexure and brush heads, and ensures thorough cleaning by maintaining maximum rigidity in tension and compression applied to the brush head while being gentle. Any material, for example, any plastic or metal, such as an inert or corrosion resistant metal such as, for example, stainless steel, or plastic coated metal, or a plastic, such as, for example, polyethylene plastic, that is sufficiently rigid and strong to firmly and detachably connect and hold the brush head piece or pieces while being flexible enough to give in to up and down motion, may be used for the flexure. The flat side or portion or area of the flexure is sized to be about as wide as the width of the eccentric box that is detachably or permanently attached to it, as described elsewhere herein, to about as wide as the width of the brush head piece, preferably about 0.1 inches to about 0.25 inches in width; and about 0.2 inches to about 2 inches in length, preferably about 0.5 to about 1 inch in length. Furthermore, the flexure is sized, dimensioned and shaped to have varying length, width and thickness throughout, depending on its design. The thickness of the flexure may vary throughout and at its flat side, may be between generally between about 0.01 inches and about 0.25 inches. The length, width and thickness of the flexure of course are also dependent on the nature of the material used for the flexure to ultimately afford optimum comfort while being flexible yet sufficiently rigid and strong to firmly hold the brush head piece.

The brush head piece of the present invention comprises two brush heads linked to each other at their bases such that the brush heads with the bristles are disposed substantially opposite each other. In addition, the single piece with dual brush heads described thus is detachably connected to said flexure where the bases of the two brush heads are linked and is adapted to pivot freely about the connection to the flexure. In one embodiment, the opposing dual brush heads may be permanently linked together at their bases such that the bristles of the two brush heads are exposed. In this embodiment, the upper and lower brush heads form a single piece. In another embodiment, the upper and lower brush heads may be separate pieces. Regardless of whether the upper and lower brush heads are linked to each other or not, they fit or lock either as a single piece or as two separate pieces to the substantially flat or flatter side of the flexure such that the brush heads can rotate or pivot independently or in tandem, respectively, substantially in the plane of the flexure where it is flat and about their point of connection to the flexure. In other words, the point of linkage to the flexure functions as a pivot for the swiveling/rotating motion of the brush heads. The brush head piece or pieces therefore rotate or pivot freely 360 degrees about the connection to the flexure. When inserted and positioned inside the mouth, the brush head piece or pieces can rotate upto 180° about the connection to the flexure.

The dual opposing brush heads, either as a single piece or as two separate pieces, are adapted to fit or lock detachably into the flexure at its flat side and may be replaceable. Therefore, once the user determines that the brush heads do not adequately perform their cleaning task, the user can replace the brush heads. Various means of removably or detachably locking or fitting the brush head piece or pieces into the flexure that are obvious to a person of ordinary skill in the art of toothbrushes and oral and dental devices are encompassed within the scope of the present invention. For example, in one embodiment, the flexure has an open loop that the brush head piece or pieces snap(s) into and lock(s) around either in the central rigid area where the bases of the brush heads are permanently linked in the single piece or in the base area of each of the individual brush head pieces. In another embodiment, the flexure has a short rigid rod extending equidistantly perpendicular to the plane of the flat side of the flexure at the end of the exposed part into which the brush head piece or pieces snap or lock into via a single or two rigid open loops present in the brush piece or pieces, respectively.

In addition, the single brush head piece or two pieces as a whole, in combination with the bristles, are sized to provide a desirable and comfortable fit closely around the upper and lower set of opposing teeth and surrounding gum area such that the brush head can oscillate up and down to clean the teeth and the gum/sulci area and once inserted and positioned into the mouth can rotate upto 180 degrees about the pivoting connection to the flexure to clean all the teeth from one side of the mouth to the other in the mouth without requiring removal from and repositioning of the toothbrush in the mouth. Accordingly, a single brush head piece may be about 0.25 inches to about 1 inch, or preferably between 0.5 inches to about 0.75 inches, or more preferably about 0.75 inches, in height. A single brush head piece may be about 0.1 inches to about 0.75 inches, or preferably between 0.25 inches to about 0.5 inches, or more preferably about 0.75 inches in width.

Separate upper and lower brush heads may be about 0.05 inches to about 0.5 inches, preferably about 0.375 inches, both in height and width.

The brush heads may comprise bristles of varying angle, thickness, firmness and length that are adapted to adequately brush and clean a pair or set of opposing upper and lower teeth as well as the nearby sulcus area and embrasures. The angles and bristle sizes are preferably selected so that the bristles of the brushes come down on each side of the teeth at an acute angle so that the bristles enter and clean the sulcus area as well as the sides of the teeth and the embrasures. For example, an angle of the brush fibers at 0-10 degrees, preferably 10 degrees, for the lower fibers and 0-45 degrees, preferably 45 degrees, for the side fibers may allow for constant contact with the teeth of the user. Such coverage is further increased by the mechanical movement of the brush head up and down caused by up and down vibration on the plane intersecting the flexure and brush head bristles which drives the bristles into the gum area thereby cleaning the hard to reach and often neglected sulci area. In one embodiment, the bristles in the upper and lower brush head are substantially identical in number, angle and/or overall shape. In another embodiment, the bristles in the upper and lower brush heads may be angled and shaped differently or may be different in number in order to custom fit the needs of the user. In one embodiment, the bristles of the upper and lower brush head are, for example, arranged to substantially contact or enclose exposed portions (sides and biting areas) of a pair or set of opposing upper and lower teeth, including the neighboring sulcus/gum area. Accordingly, in one embodiment, each of the opposing brush heads is made up of a group of bristles formed in a "U" shape encapsulated in the head. The bristles in the brush heads may be arranged, for example, to substantially surround or fit closely around the exposed portions of a pair or set of opposing upper and lower teeth and the adjacent gum areas.

In one embodiment, a grommet fits over the handle to link the flexure and the handle. The handle houses an eccentric drive box or block, which is described as an enclosed shell elsewhere herein, into which one end of a single, substantially rigid drive shaft extends. The end of the drive shaft has an eccentric weight that extends into the eccentric box. The eccentric weight is an off center weight. In other words, the eccentric weight is offset from the centerline of the driving shaft. The eccentric weight has a dual purpose. The fact that it is off center from the centerline of the driving shaft forces the flexure up and down. In addition, the fact that it is off balanced adds inertia to the force being applied to the flexure. The flexure and the substantially rigid drive shaft are arranged in a direction that is substantially along the axis of the handle. The eccentric drive box or block is located inside the handle to facilitate rotation of the eccentric weight connected to the drive shaft inside the eccentric box or block. Inside the handle, the flexure is permanently or detachably affixed or attached to a side of the eccentric drive box or block at its substantially flat or planar side in the unexposed portion extending into the handle. The rigid drive shaft is linked to a motor on the other end inside the handle housing with one end linked to the eccentric weight and extending into the eccentric box or block as described herein. The motor can be operated either via direct power or using a battery. In other words, the toothbrush may be battery operated or may be operated by plugging it into an electrical power source. In the embodiment where the motor is battery operated, the battery is housed inside the handle. In the embodiment where the toothbrush may be plugged into an electrical power source, an electrical cord connected to the motor with a plug pin at its free end extends outward from the handle, preferably from the base of the handle.

When the motor is turned on using a switch that is located on the outside portion of the handle, it revolves and the connected drive shaft rotates and therefore the eccentric weight rotates inside the eccentric box or enclosed shell, and transmits oscillating vibration via the flexure to the brush heads. When the toothbrush is activated, the shaft operates to transmit the oscillating up and down motion to the brush heads.

The devices of the present invention may further include in the handle housing, an electronics board that automatically gives the user an appropriate time frame for brushing teeth. The automatic time sensor may include an audible alert to signal that sufficient time has elapsed.

The devices of the invention may further include a fluid delivery system that delivers fluid to the brush heads to enhance the cleaning ability. The fluids delivered include water and antiseptic solutions. In addition, the devices may include a line to evacuate the fluids from the user's mouth.

Further means may be provided for cleaning the top or biting surfaces of the teeth as well as the sides of the teeth, which include means to drive the bristles.

More particularly, there is provided, in one embodiment, an oral cleaning device which comprises a brush head piece, a flexure, and a handle, wherein the flexure is connected to the brush head piece at one end and the handle at the other end. The brush head piece comprises two brush heads, wherein each of the two brush heads have a base and the two brush heads are linked to each other at their respective bases, such that the brush heads are disposed substantially opposite each other. The brush head piece is detachably connected to the flexure at the point where the bases of the brush heads are linked and is adapted to pivot freely about the connection to the flexure. Preferably, the flexure is a substantially flat piece, and is adapted to permit up and down movement in the plane of the flexure and brush heads. Because of this unique construction, all teeth of a user can be cleaned without removing the device from the mouth of a user and repositioning it. The flexure preferably comprises an exposed part where it is connected to the brush head piece and an unexposed part extending into the handle. The unexposed part of the flexure is substantially planar.

An eccentric box is provided, to which the flexure is affixed. A rigid drive shaft has first end connected to an off-center weight that extends into the eccentric box, and is linked at a second end to a motor. A power source is connected to the motor, wherein the eccentric box, the eccentric weight, rigid drive shaft, a portion of the flexure and the motor are all housed in the handle.

Rotation of the drive shaft transmits an up and down oscillating vibration to the brush heads via the flexure, to permit effective brushing of the teeth and stimulation of the gum area of a user. The bristles of both of the brush heads are adapted to substantially contact and fit around a pair or set of opposing upper and lower teeth of a user simultaneously. In one preferred embodiment, the bristles are angled between 0° and 45°.

In some embodiments of the invention, a fluid delivery line is provided. Water, an antiseptic solution, or other suitable fluid may be supplied to the user's mouth through the fluid delivery line. A suction line may also be provided, as well as one or more of a timing device and an alarm. A drive system may be provided for moving the brush bristles.

The invention, together with additional features and advantages thereof, may best be understood by reference to the following description taken in conjunction with the accompanying illustrative drawings.

DESCRIPTION OF THE PREFERRED EMBODIMENTS

Figure 1:
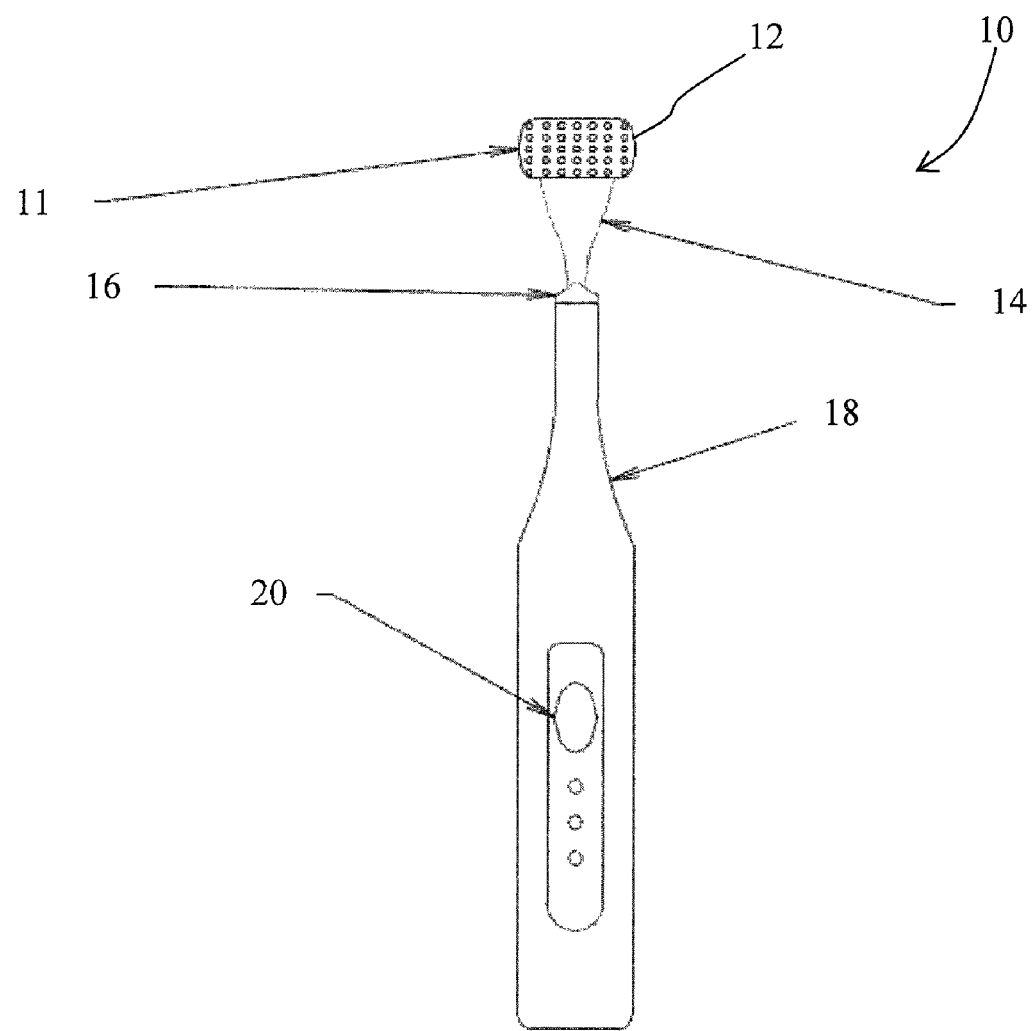
FIG. 1 is a top view of an oscillating toothbrush constructed in accordance with one embodiment of the present invention.
Figure 2:
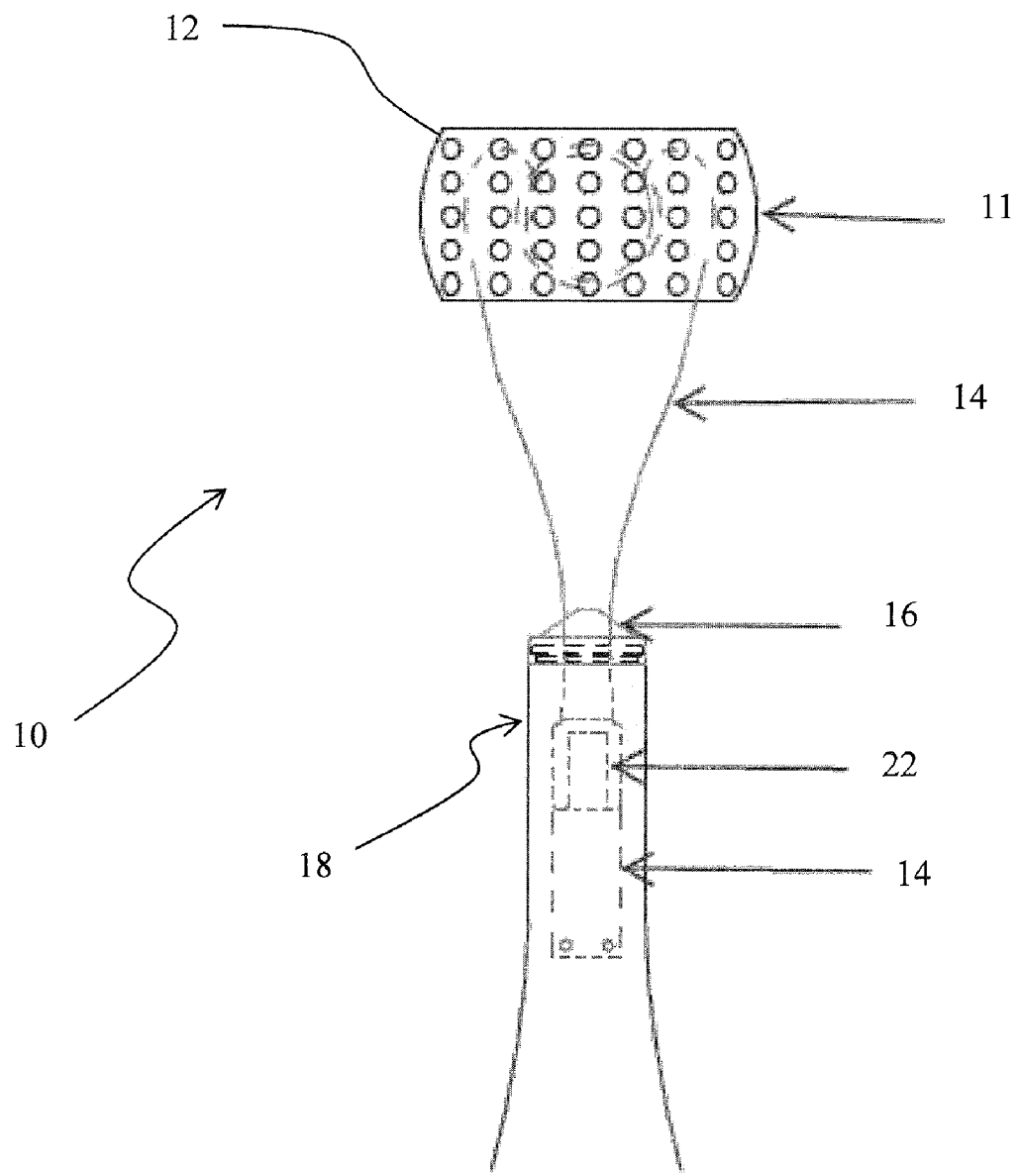
FIG. 2 is a view of the flexure in FIG. 1 extending inside the handle.
Figure 3:
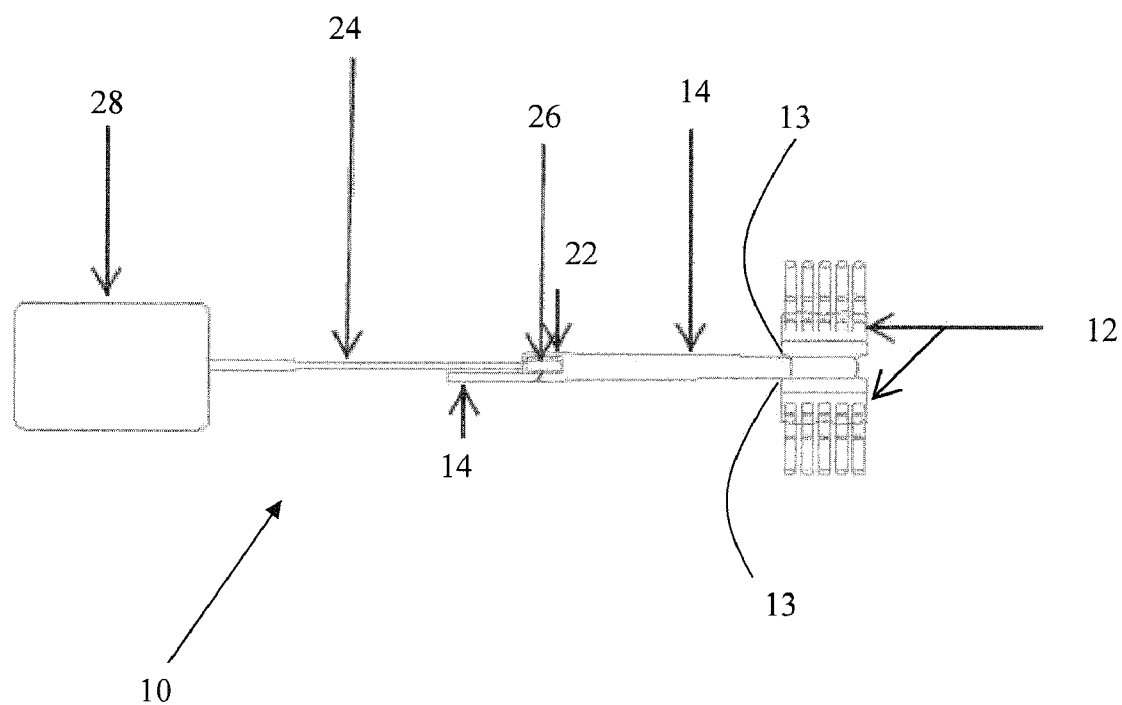
FIG. 3 is a perpendicular cross-sectional view of an oscillating toothbrush in accordance with FIG. 1

Referring now more particularly to the drawings, there is shown in FIGS. 1-3 two perpendicular top views of an oscillating toothbrush 10. As shown in both FIG. 1 and FIG. 3, the toothbrush 10 comprises dual opposing brush heads 12 in a single brush head piece 11 which are connected to each other at their respective bases 13 as shown in FIG. 3 and detachably connected at this point of linkage to a flexure 14. The flexure 14 is a generally flat piece and comprises a part that is exposed where it is detachably linked to the upper and lower brush heads, and a part where it extends via a grommet 16 into the handle 18 (unexposed parts not shown in FIG. 1, but shown in FIG. 2). The grommet 16 fits over the handle 18. The brush heads fit or lock to respective, opposing flatter sides 19a, 19b (FIG. 5) of the flexure 14 such that the brush heads can rotate or pivot in tandem substantially in the plane of each of the flatter sides of the flexure and about the point of linkage of the bases of the brush heads to the flexure 14. FIG. 1 is a top view of the tooth brush that shows the flatness of the flexure 14 and FIG. 3 is a top view of the tooth brush that shows the thickness of the flexure 14. Also shown in FIG. 1 is power switch 20.

FIG. 2 shows how the flexure extends via grommet 16 inside handle 18. Also shown in FIG. 2 is the upper side of an eccentric box 22 that is attached either permanently or detachably to a substantially flat or planar portion of flexure 14 that extends inside the handle and therefore is not normally seen when a user is regularly operating the toothbrush.

Figure 8:
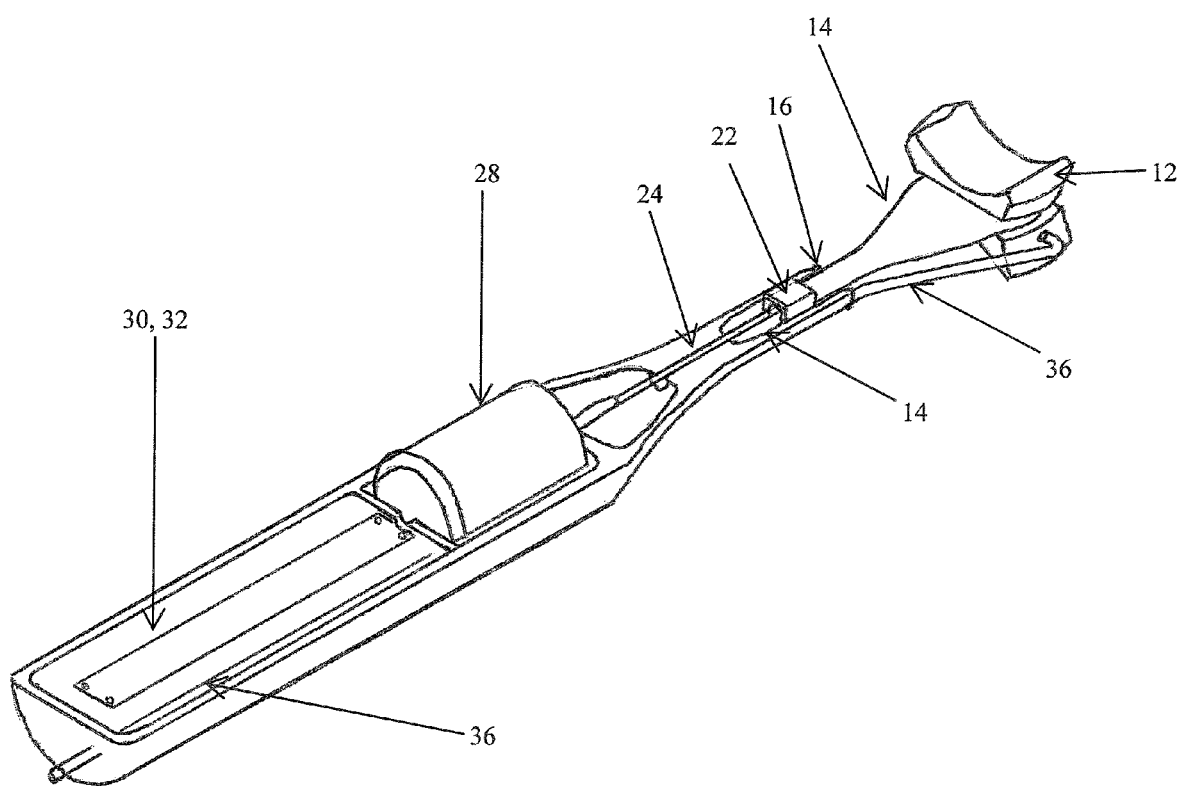
FIG. 8 is a cross-sectional view of an oscillating toothbrush with a brush head in accordance with FIG. 7 and with a fluid delivery line.

FIG. 3 shows a cross sectional view of an oscillating toothbrush shown in FIG. 1. As seen in FIGS. 2 and 3, inside the upper portion of the handle 18, the flexure is permanently affixed or attached to a side of the eccentric drive box or block 22 at a part or portion or area or side that is substantially flat or planar. The grommet 16 fits over the handle 18. The handle 18 houses an eccentric drive box or block, into which one end of a single, substantially rigid drive shaft 24 extends. The end of the drive shaft 24 that extends into the eccentric box 22 has an eccentric weight 26. The eccentric weight 26 is offset from the centerline of the drive shaft and forces the flexure up and down. The eccentric weight is off balance to add inertia to the force being applied to the flexure. The flexure 14 and the substantially rigid drive shaft 24 are arranged in a direction that is substantially along the axis of the handle 18. The eccentric drive box or block 22 is located inside the grommet 16 to facilitate rotation of the drive shaft 24 inside the eccentric box or block 22 and thereby, rotation or movement of the eccentric weight 26 inside the box or block. The rigid drive shaft 24 is linked to a motor 28 on the other end inside the handle housing with one end extending into the eccentric box or block 22 with the off center eccentric weight connected to its end as described herein. In this embodiment, the motor 28 is operated using a power source 30 (battery) housed inside the handle 18. Also included is an electronic chip 32 that is used for a timer with an alarm. Elements 30 and 32 are shown in FIG. 8.

When the motor 28 is turned on, using a switch 20 that is located on the outside portion of the handle (shown in FIG. 1), it revolves and the connected drive shaft 24 and therefore the eccentric weight 26 that is linked to the end of the shaft rotates inside the eccentric box 22, and transmits oscillating vibration via the flexure 14 to the brush heads 12. When the toothbrush 10 is activated, the shaft 24 operates to transmit oscillating up and down motion to the brush heads 12.

Figure 4:
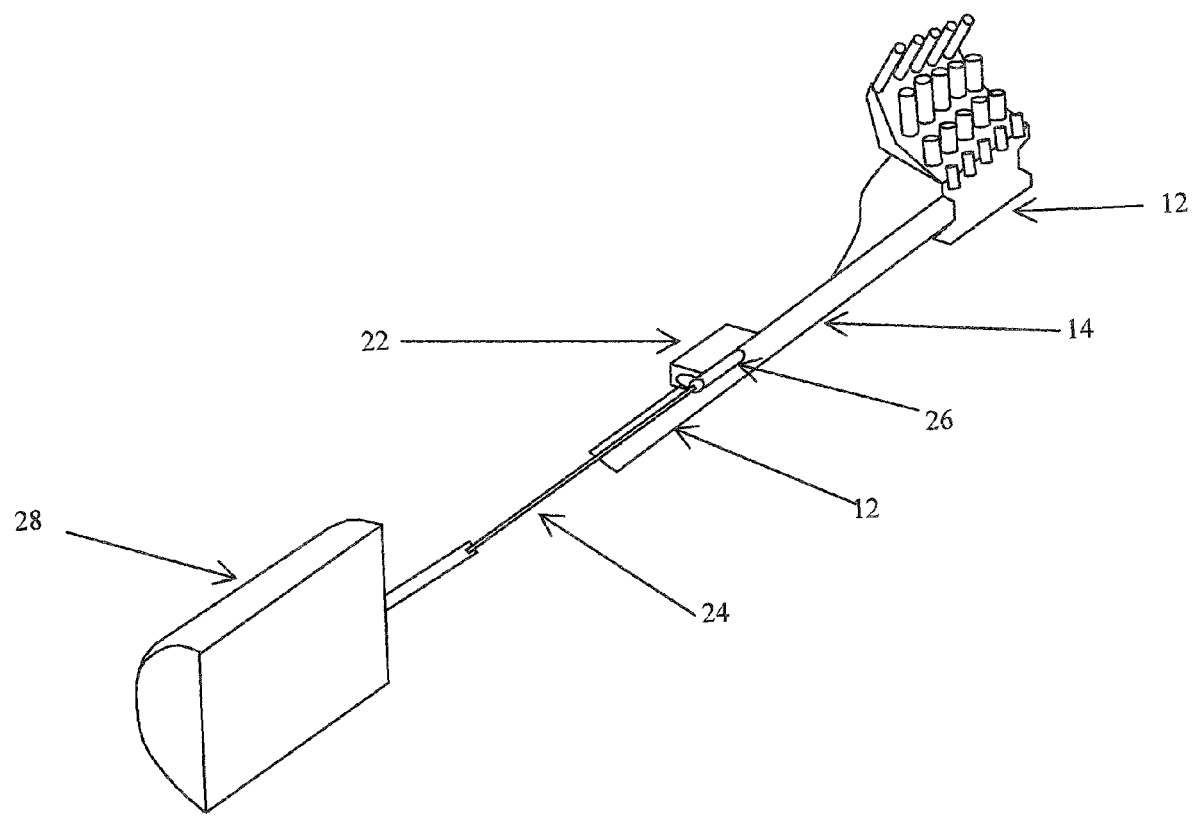
FIG. 4 is a cross-sectional view of the connection of the flexure to the brush head and eccentric box and motor in accordance with FIG. 1 and FIG. 3.

FIG. 4 shows a perspective view of the entire flexure 14, including the areas not exposed to the user once assembled, and the eccentric box 22, drive shaft 24 and motor 28. In this figure, the flexure 14 is shown as being permanently affixed or attached to a side of the eccentric drive box or block 22 at its substantially flat or planar side or portion and further extending parallel to the drive shaft 24. The other end of the flexure 14, which is the exposed portion extending out of the grommet 16 (FIGS. 1 and 2) detachably connects to the brush heads 12. Shown extending into the eccentric drive box or block 22, is the rigid drive shaft 24 with an off center eccentric weight connected to the end of the shaft and extending into the eccentric drive box 22. As seen, the flexure 14 and the substantially rigid drive shaft 24 are substantially parallel to each other and are arranged in a direction that is generally along the axis of the handle 18. The rigid drive shaft 24 is linked to the motor 28 on the other end.

Figure 5:
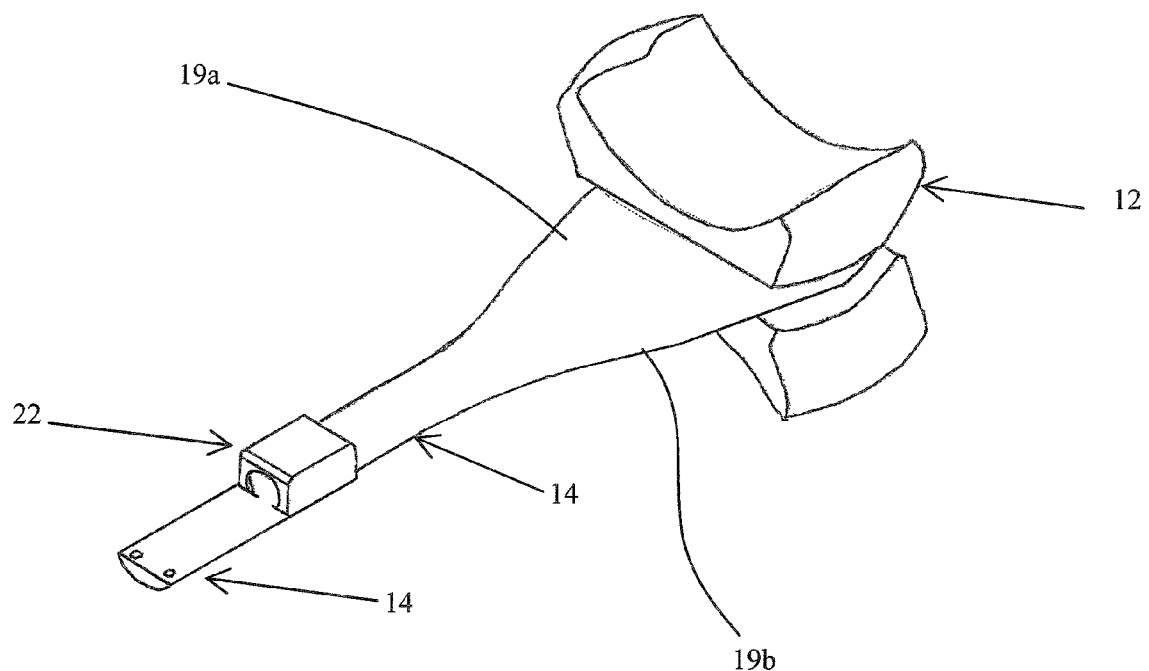
FIG. 5 is a view of the connection of the flexure to the brush head and eccentric box in accordance with FIG. 4.
Figure 6:
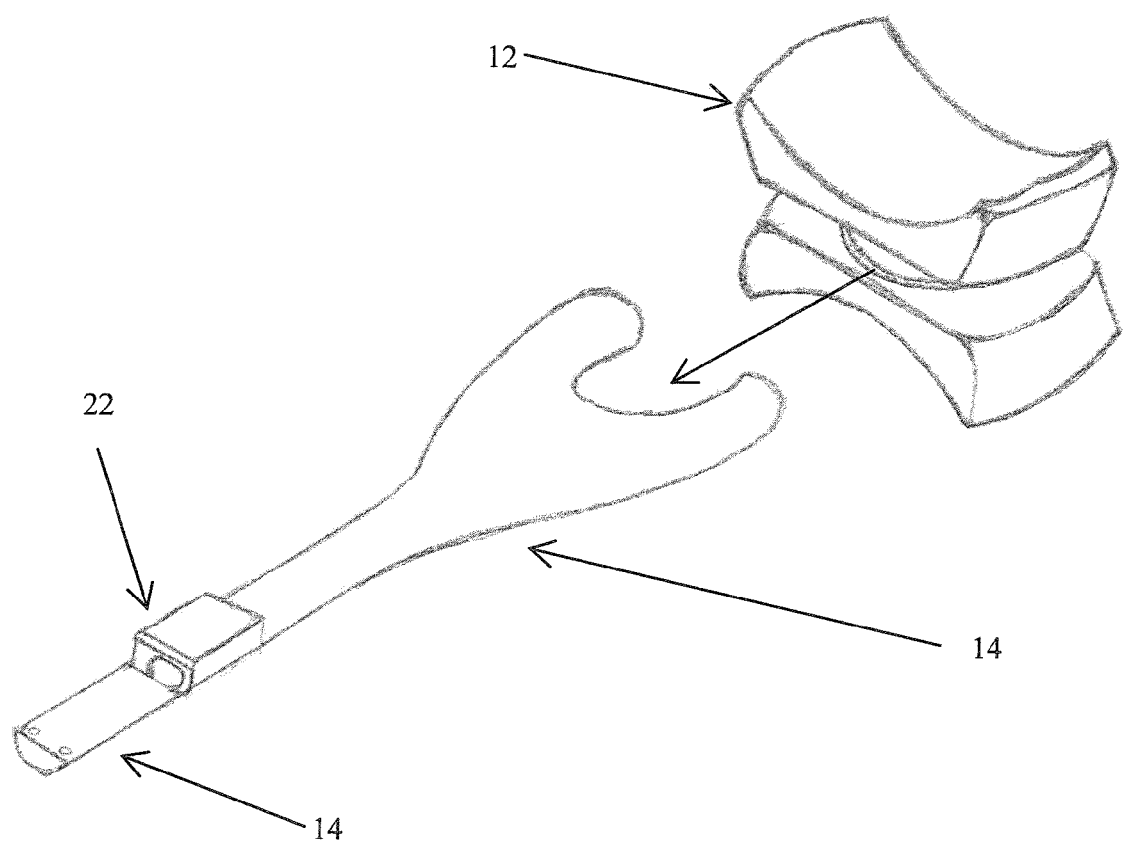
FIG. 6 is a view of the connection of the flexure to the brush head and eccentric box in accordance with FIG. 5 wherein the brush head component is detached from the flexure.

FIG. 5 illustrates the connection of the flexure 14 to the brush head 12 and eccentric box 22 in accordance with FIG. 4. FIG. 6 is a view of the connection of the flexure 14 to the brush head 12 and eccentric box 22 in accordance with FIG. 5, wherein the brush head component 12 is detached from the flexure.

In this embodiment is shown one means of detachably connecting the flexure 14 to the brush heads 12. However, the present invention encompasses other means of detachably connecting the brush head piece to the flexure that are obvious to a person of ordinary skill in the art.

Figure 7:
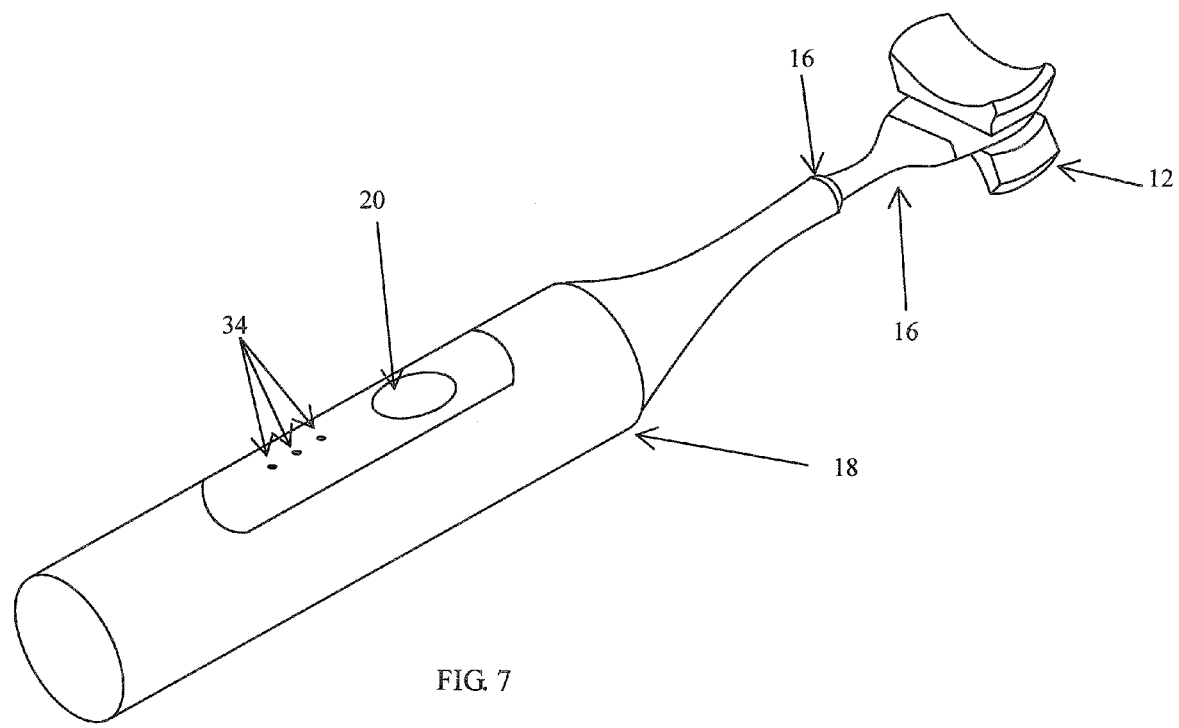
FIG. 7 is a perspective view of an oscillating toothbrush with a brush head in accordance with one embodiment of the present invention.

Illustrated in FIG. 7 is a perspective view of an oscillating toothbrush with a brush head configuration in accordance with one embodiment of the present invention. Shown in FIG. 7 are indicator lights 34.

In FIG. 8, there is illustrated a perspective view of an oscillating toothbrush with a brush head configuration in accordance with one embodiment of the present invention. Included in this figure is a fluid delivery line 36 that extends out from the base of the toothbrush handle 18 to be connected to a fluid source such as a drinking water faucet or a container with an antiseptic solution.

All of the terms used herein are descriptive rather than limiting, and many changes, modifications, and substitutions may be made by one having ordinary skill in the art without departing from the spirit and scope of the invention, which is to be limited only in accordance with the following claims. For example, one such modification would be to substitute an electromagnetic radiation (EMR) power source, such as that utilized in the Pulsonic Model 3715 manufactured by Braun under the trademark ORAL-B for the motor drive shown and described herein, for the purpose of driving the brush heads 12.

What is claimed is:

1. An oral cleaning device comprising:
    a brush head piece, a flexure, and a handle wherein said flexure is connected to said brush head piece at one end and said handle at the other end;
    said brush head piece comprising two brush heads, each of said two brush heads having a base and the two brush heads being linked to each other at their respective bases such that the brush heads are disposed substantially opposite each other, said brush head piece being detachably connected to the flexure at the point where the bases of the brush heads are linked and being adapted to pivot freely about the connection to the flexure.

2. The device of claim 1 wherein the flexure is a substantially flat piece.

3. The device of claim 1 wherein the flexure is adapted to permit up and down movement in the plane of the flexure and brush heads.

4. The device of claim 1 wherein all teeth of a user can be cleaned without removing the device from the mouth of a user and repositioning it.

5. The device of claim 1 wherein the flexure comprises an exposed part where it is connected to the brush head piece and an unexposed part extending into the handle.

6. The device of claim 5 wherein the unexposed part of the flexure is substantially planar.

7. The device of claim 1 and further comprising an eccentric box to which said flexure is affixed;
    a rigid drive shaft having a first end connected to an off-center weight that extends into the eccentric box;
    a motor to which a second end of the rigid drive shaft is linked; and
    a power source connected to the motor, wherein the eccentric box, the eccentric weight, rigid drive shaft, a portion of the flexure and motor are housed in the handle.

8. The device of claim 7 wherein rotation of the drive shaft transmits an up and down oscillating vibration to the brush heads via the flexure to permit effective brushing of the teeth and stimulation of the gum area of a user.

9. The device of claim 1 wherein the bristles of both of said brush heads are adapted to substantially contact and fit around a pair or set of opposing upper and lower teeth of a user simultaneously.

10. The device of claim 1 wherein the bristles are angled between 0° and 45°.

11. The device of claim 1 and further comprising a fluid delivery line.

12. The device of claim 11 wherein water flows through the fluid delivery line.

13. The device of claim 11 wherein an antiseptic solution flows through the delivery line.

14. The device of claim 11 and further comprising a suction line.

15. The device of claim 1, and further comprising a timing device and alarm.

16. The device of claim 1 and further comprising a drive system for moving the bristles.

* * * * *